United States Patent [19]

Rogers-Evans et al.

[11] Patent Number: 5,670,640

[45] Date of Patent: Sep. 23, 1997

[54] PROCESS FOR THE MANUFACTURE OF IMIDAZODIAZEPINE DERIVATIVES

[75] Inventors: Mark Rogers-Evans, Ettingen; Paul Spurr, Riehen, both of Switzerland

[73] Assignee: Hoffmann-La Roche Inc., Nutley, N.J.

[21] Appl. No.: 762,632

[22] Filed: Dec. 9, 1996

[30] Foreign Application Priority Data

Feb. 2, 1996 [EP] European Pat. Off. .............. 96101494

[51] Int. Cl.[6] .................................................. C07D 243/14
[52] U.S. Cl. .................................................. 540/498
[58] Field of Search ...................................... 540/498

[56] References Cited

U.S. PATENT DOCUMENTS

| | | | |
|---|---|---|---|
| 4,051,127 | 9/1977 | Krausz | 260/239.3 D |
| 4,187,306 | 2/1980 | Mayer et al. | 424/251 |
| 4,316,839 | 2/1982 | Gerecke et al. | 260/239.3 T |
| 4,595,531 | 6/1986 | Milkowski et al. | 260/239 BD |
| 5,536,832 | 7/1996 | Andrasi et al. | 540/557 |
| 5,604,223 | 2/1997 | Andrasi et al. | 514/220 |

*Primary Examiner*—Joseph McKane
*Attorney, Agent, or Firm*—George W. Johnston; Ellen Ciambrone Coletti; Robert A. Silverman

[57] ABSTRACT

A process for the manufacture of compounds of formula

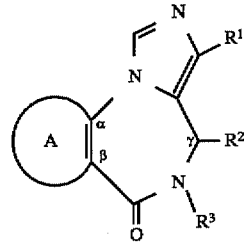

13 Claims, No Drawings

PROCESS FOR THE MANUFACTURE OF IMIDAZODIAZEPINE DERIVATIVES

BACKGROUND OF THE INVENTION

U.S. Pat. No. 4,316,839, incorporated herein by reference, describes processes for manufacturing compounds of formula

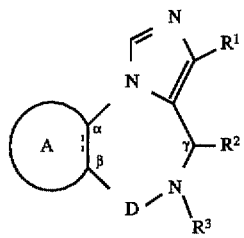

A wherein A together with the two carbon atoms denoted as α and β is selected from the group consisting of

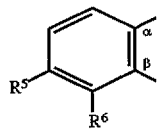

(a)

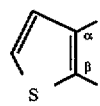

(b)

and

(c)

the dotted line represents the double bond present in groups (a) and (b), D is
>C=O or >C=S, $R^1$ is selected from the group consisting of cyano, lower alkanoyl and a group of the formula —COOR$^4$, $R^4$ is selected from the group consisting of methyl, ethyl, isopropyl and 2-hydroxyethyl, $R^5$ is selected from the group consisting of hydrogen, trifluoromethyl and halogen and $R^6$ is selected from the group consisting of hydrogen, trifluoromethyl, halogen and lower alkyl and either $R^2$ is hydrogen and $R^3$ is hydrogen or lower alkyl or $R^2$ and $R^3$ together are trimethylene or propenylene and the carbon atom denoted as γ has the S- or R,S-configuration.

For example U.S. Pat. No. 4,316,839 describes reacting a compound of the formula

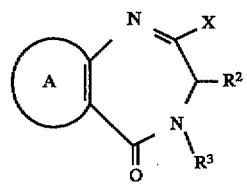

II wherein A, $R^2$ and $R^3$ are as described above and X is a halogen atom, with an isocyanoacetic ester. In accordance with such process, compounds of formula A in which $R^1$ represents a lower alkyl ester can be manufactured from compounds of formula II, in which X represents a leaving group, and an alkyl isocyanoacetate. The reaction is carried out in an inert solvent and in the presence of a base at a temperature between about −40° C. and about room temperature.

The compounds of formula A, are known as pharmaceutically active substances. It has been shown that they have a pronounced affinity to the central benzodiazepine receptors and are capable of antagonising the central-depressant, muscle relaxant, ataxic, blood pressure-lowering and respiratory-depressant properties of 1,4-benzodiazepines which have tranquilizing activity.

BRIEF SUMMARY OF THE INVENTION

The invention relates to a process for the manufacture of imidazodiazepine derivatives of formula

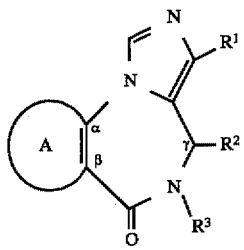

I wherein

A together with the two carbon atoms denoted as α and β is one of the groups

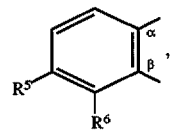

(a)

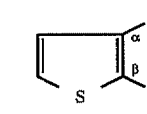

(b)

or

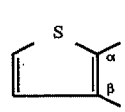

(c)

$R^1$ is cyano or a group of the formula —COOR$^4$,
$R^2$ is hydrogen,
$R^3$ is lower alkyl, or
$R^2$ and $R^3$ together are a di- or a trimethylene group,
$R^4$ is lower alkyl or benzyl; and
$R^5$, $R^6$ each independently are hydrogen, halogen, trifluoromethyl, lower alkoxy or nitro;
and the carbon atom denoted by γ has the S-configuration when $R^2$ is different from hydrogen.

More particularly, the invention relates to a process for the manufacture of compounds of the formula I which process comprises reacting a compound of the formula II in the presence of a base with a compound of the formula

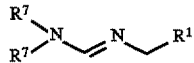

III wherein $R^7$ is lower alkyl or cycloalkyl and $R^1$ is as described above for formula I.

Thus, according to the present invention compounds of formula I are manufactured by reaction of a compound of the formula II with (dialkylamino-methyleneamino)-acetic acid alkyl ester or (dialkylamino-methyleneamino)-nitrile.

To use these compounds in place of isocyanoacetic ester as described in U.S. Pat. No. 4,316,839 is an economical and more convenient process on ecological and toxicological grounds.

DETAILED DESCRIPTION OF THE INVENTION

As used herein, the term "lower alkyl" denotes a straight or branched chain saturated hydrocarbon group containing at most 7, preferably 1–4 carbon atoms such as methyl, ethyl, n-propyl, isopropyl, n-butyl, sec.-butyl and the like. The term "lower alkoxy" denotes a lower alkyl ether group in which the lower alkyl group is as described above, for example, methoxy, ethoxy, propoxy, pentoxy and the like.

The term "halogen" means fluorine, chlorine, bromine and iodine.

For compounds of formula I, $R^1$ preferably is cyano or a group of the formula —$COOR^4$ in which $R^4$ preferably is ethyl.

For compounds of formula I, when $R^2$ is hydrogen, then $R^3$ preferably is methyl.

For compounds of formula I, the symbol A preferably is the group (a). In this group (a), $R^5$ preferably is hydrogen or fluorine and $R^6$ preferably is hydrogen, fluorine, chlorine or methyl with at least one of $R^5$ and $R^6$ preferably is hydrogen.

Compounds of formula I which are prepared by the above mentioned process are especially preferred, wherein A denotes a group (a), $R^5$ denotes fluoro, $R^6$ denotes hydrogen and $R^1$ represents a cyano group or the group —$COOC_2H_5$.

Compounds of formula I which are especially preferred are:

Ethyl-8-fluoro-5,6-dihydro-5-methyl-6-oxo-4H-imidazo[1,5-a][1,4]-benzodiazepine-3-carboxylate and 8-fluoro-5-methyl-6-oxo-5,6-dihydro-4H-imidazo[1,5-a][1,4]benzodiazepine-3-carbonitrile.

The process as described below is shown in Scheme 1.

Scheme 1

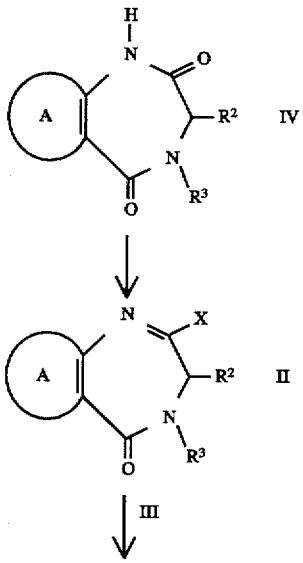

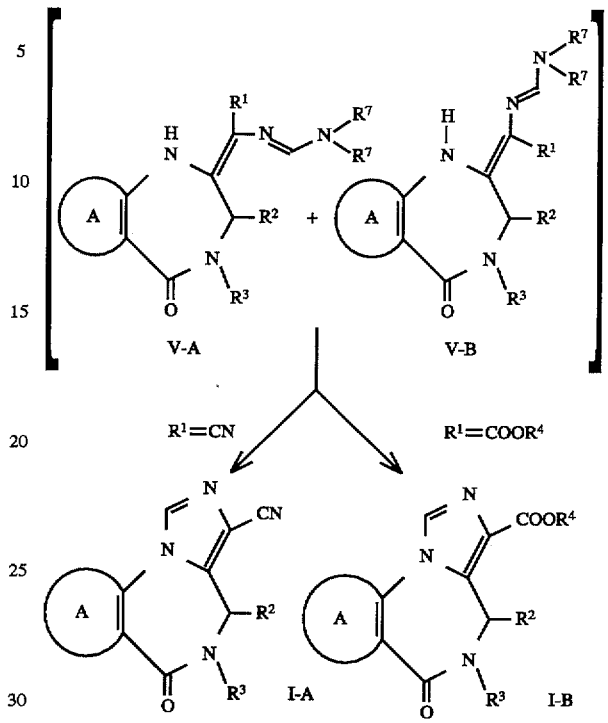

wherein A, $R^1$, $R^2$, $R^3$, $R^4$ and $R^7$ are described as above and X is a halogen atom, preferably chlorine.

The reaction of a compound of formula II with a compound of formula III is carried out in tetrahydrofuran, toluene or any other suitable inert organic solvent and at a temperature between about –40° C. and –30° C.

Suitable bases are n-butyllithium, alkali metal alkoxides, alkali metal hydrides, alkali metal amides such as lithium amides or lithium diisopropyl-amide or tertiary amines such as triethylamine.

The reaction is conveniently carried out with lithiumhexamethyldisilazide which can be prepared in situ from n-butyllithium and 1,1,1,3,3,3-hexamethyl-disilazane. In the following paragraphs, the reaction is described in more detail.

A solution containing 1,1,1,3,3,3-hexamethyl-disilazane, n-butyllithium and a compound of formula III, for example, (dimethylamino-methylene-amino)-acetic acid ethyl ester or (dimethylamino-methyleneamino)-nitrile, is treated with a solution containing a compound of the formula II and N,N-dimethyl-p-toluidine at about –30° to –40° C.

There are obtained intermediates with an open ting structure of formula V-A and V-B. Cyclisation of these compounds produces compounds of formulae I-A or I-B. The cyclisation can be carried out in the presence of an acid, for example, acetic acid.

Compounds of formula II can be obtained by reaction of a compound of formula IV with phosphorous oxychloride to obtain a compound of formula II. This compound can be used in situ or be isolated to form a compound of formula I as described above. The manufacture of compounds of formula I is described in Examples 1–4 in more detail. Compounds of formula IV and compounds of formula III are known compounds, or analogues of known compounds, and can be manufactured by well known methods.

The following Examples are given by way of illustration only, but are not to be construed as limiting.

EXAMPLE 1

2-Chloro-7-fluoro-4-methyl-3,4-dihydro-benzo[e][1,4]diazepine-5-one a) A mixture of 20.8 g (100 mmol) 7-fluoro-4-methyl-3,4-dihydro-1H-benzo[e][1,4]diazepine-2,5-dione, 38 ml (263 mmol) N,N-dimethyl-p-toluidine and 200 ml toluene were stirred and heated to 100° C. and then were treated dropwise with 10.2 ml (110 mmol) phosphorous oxychloride within 20 minutes. The solution was stirred for 2 hours at 100° C., then cooled to 5°–10° C. and poured into a stirring solution of 48 g $K_2CO_3$ in 150 ml water and 50 g ice. The mixture was filtered and the filtrate was separated. The organic phase was washed with water, filtered and the filtrate was evaporated to give a residue of oily crystals. The residue was then evaporated in high vacuo to dryness.

Yield: 58.71 g of crude product (oil).

b) Isolation of the free title compound:

To the yielded 2-chloro-7-fluoro-4-methyl-3,4-dihydro-benzo[e][1,4]-diazepine-5-one containing N,N-dimethyl-p-toluidine was added 50 ml isopropylether. The solution was stirred under an atmosphere of argon for 30 minutes at room temperature, whereafter 20 ml hexane was added dropwise over 15 minutes. The reaction mixture was stirred for 30 minutes at room temperature and then for 1 hour at 0°–5° C. The crystals were separated and washed with 50 ml of a cold mixture of solvents and then dried in high vacuum to give the title compound as orange crystals.

Yield: 19.32 g (85,5%)

Purity: 97%

EXAMPLE 2

Ethyl-8-fluoro-5,6-dihydro-5-methyl-6-oxo-4H-imidazo[1,5-a][1,4]benzodiazepine-3-carboxylate
(via isolated iminochloride)

A solution of 24 ml (115 mmol) 1,1,1,3,3,3-hexamethyl-disilazane in 300 ml tetrahydrofuran was stirred and cooled to −35° C. At this temperature there was added dropwise 69 ml (110 mmol) n-butyllithium over 45 minutes. The mixture was stirred 30 minutes at −35° C. and then a solution of 15.82 g (100 mmol) (dimethylamino-methylenamino)-acetic acid ethyl ester in 50 ml THF was added dropwise over 1 hour. The solution was stirred at −35° C. for 30 minutes.

Separately, 12.02 g (50 mmol) of 2-chloro-7-fluoro-4-methyl-3,4-dihydro-benzo[e][1,4]diazepine -5-one were dissolved in 100 ml tetrahydrofuran and 2.9 ml (20 mmol) N,N-dimethyl-p-toluidine and stirred under an atmosphere of argon. This solution was immediately added dropwise at −35° to −40° C. over 70 minutes to the solution obtained according to the preceding paragraph. The resulting mixture was stirred at −35° C. for 2 hours.

A solution of 15 ml (260 mmol) acetic acid in 10 ml tetrahydrofuran was added dropwise at −35° to −40° C. over 20 minutes to the mixture obtained above.

The reaction mixture was stirred over night at room temperature. Thereafter was added dropwise 5 ml acetic acid and the reaction mixture was refluxed for 6 hours. The resulting reaction mixture was allowed to cool to room temperature, whereafter it was concentrated on the rotary evaporator at 35° C.

100 ml heptane was added and the mixture again concentrated. An additional 100 ml heptane was added and the mixture stirred at 35° C. for 30 minutes.

The reaction mixture was then left to cool at 0° C. overnight. The crystals were filtered and washed with 100 ml cold heptane and then stirred in a solution of 150 ml methylene chloride and 100 ml 5% $NaHCO_3$ for 5 minutes and then the layers were separated. The organic phase was extracted two times with water (100 ml) and the resulting water phases were washed two times with methylene chloride.

The combined organic extracts were concentrated and then dried at reduced pressure at 35° C.

Yield of the crude product: 16.68 g

Purity: 86%.

The crude product was then dissolved and refluxed in 170 ml ethanol, stirred over night at room temperature and then left for 4 hours at 0° and 2 hours at −20° C. The crystals were filtered and washed with 50 ml of cooled (−20°) ethanol.

Yield: 14.73 g of white crystals (98%),

Mp: 201°–202° C.

Purity: 99%.

EXAMPLE 3

Ethyl-8-fluoro-5,6-dihydro-5-methyl-6-oxo-4H-imidazo[1,5-a][1,4]benzodiazepine-3-carboxylate
(via non-isolated iminochloride)

a) 48 ml (230 mmol) of 1,1,1,3,3,3-hexamethyl-disilazane were dissolved in 300 ml tetrahydrofuran. The solution was cooled to 0° C. and then was added dropwise 138 ml (220 mmol) n-butyllithium within 20 minutes. The reaction mixture then was stirred at 0° C. for 30 minutes and cooled to −35° C., whereafter a solution of 31.6 g (200 mmol) (dimethylamino-methyleneamino)-acetic acid ethyl ester in 100 ml tetrahydrofuran was added dropwise within 60 minutes. After stirring at −35° C. for 30 minutes, 58.71 g (≦100 mmol) 2-Chloro-7-fluoro-4-methyl-3,4-dihydro-benzo[e][1,4]diazepine -5-one, obtained in Example 1a) above, was dissolved in a solution of 200 ml tetrahydrofuran containing 0.2 ml N,N-dimethyl-p-toluidine and added dropwise to the obtained reaction mixture within 1 hour. This mixture was then stirred for 2.5 hours at −35° to −40° C., then treated dropwise with 40 ml acetic acid dissolved in 40 ml tetrahydrofuran. The mixture (pH 6) was warmed to room temperature then refluxed for 2 hours. After cooling to room temperature overnight, it was concentrated on a rotary evaporator at 40° C. to remove most of the THF (not to dryness).

150 ml heptane was added to the residue and it was concentratred again. After a further addition of 150 ml heptane the mixture was rotated at 0°–5° C. for 60 minutes without vacuum. The crystals were filtered, washed with 100 ml of cold heptane and then partitioned between a solution of 250 ml methylene chloride and 200 ml 5% $NaHCO_3$. After stirring for 5 minutes the layers were separated. The organic phase was extracted twice with 100 ml water and the resulting water phases were back extracted 2 times with 70 ml methylene chloride. The combined organic extracts were concentrated on a rotary evaporator at 35° C. and the residue obtained was dried at 40° C./20 mbar.

Yield of the crude product: 26.78 g,

Purity: 83.5%

The crude product was refluxed in 260 ml ethanol, stirred over night at room temperature and 4 hours at 0° C. and then the crystals were filtered off and washed with 70 ml cold ethanol and dried at 40°/20 mbar.

Yield of the white crystals: 20.6 g (68%)

Purity: 96%,

Mp: 196°–197° C.

EXAMPLE 4

8-Fluoro-5-methyl-6-oxo-5,6-dihydro-4H-imidazo[1,5-a][1,4]benzodiazepine-3-carbonitrile a) A solution of 4.8 ml (23 mmol) 1,1,1,3,3,3-hexamethyldisilazane in 40 ml toluene was cooled to 0° C. and was treated dropwise with 13.8 ml (22 mmol) n-butyllithium over 10 minutes. The solution was stirred and cooled to –35° C. and treated with 1.7 g (12 mmol) (dimethylaminomethyleneamino)-acetonitrile in 5 ml toluene over 20 minutes.

Separately, 2.3 g (10 mmol) of 2-chloro-7-fluoro-4-methyl-3,4-dihydro-benzo[e][1,4]diazepin-5-one were dissolved in a mixture of 25 ml toluene, 5 ml THF and 0.7 ml (5 mmol) N,N-dimethyl-p-toluidine and stirred under an atmosphere of argon. This solution was immediately added dropwise at –35° C. within 35 minutes to the above mixture. The resulting mixture was stirred at –35° C. for 2.5 hours. A solution of 5 ml acetic acid in 5 ml toluene was added dropwise at –35° C. The reaction mixture (pH 5) was stirred at room temperature over night and then refluxed for 30 minutes whereafter it was concentrated on a rotary evaporator at 35° C. Then 25 ml n-heptane was added to the reaction mixture and the solution was rotated at room temperature for 30 minutes. The brown mixture was filtered and washed with 10 ml n-heptane and the resultant gum was partitioned between (50 ml) methylene chloride and (30 ml) water. The organic phase was filtered and then extracted with two further portions of (30 ml) water, dried over sodium sulphate, treated with (2.0 g) silica, filtered, evaporated and dried at room temperature under high vacuum.

Yield of the crude product: 1.85 g

Purity: 72%.

The crude compound obtained above was recrystallized from 40 ml ethanol. The reaction mixture was cooled to 0° C. and stirred for 2 hours. The obtained crystals were filtered, washed with cold ethanol and dried over night at 40° C./20 mbar.

Yield: 1.10 g (42%)

Purity: 98%.

We claim:

1. A process for the manufacture of a compound of formula I

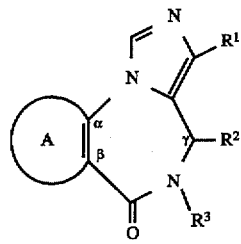

wherein
A together with the two carbon atoms denoted as α and β is one of the groups

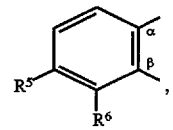

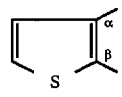

or

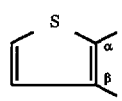

$R^1$ is cyano or a group of the formula —COOR$^4$,
$R^2$ is hydrogen,
$R^3$ is lower alkyl, or
$R^2$ and $R^3$ together are a di- or trimethylene group,
$R^4$ is lower alkyl or benzyl; and
$R^5$, $R^6$ each independently are hydrogen, halogen, trifluoromethyl, lower alkoxy or nitro
and the carbon atom denoted by γ has the S-configuration when $R^2$ is different from hydrogen, which process comprises reacting a compound of the formula

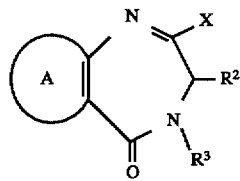

wherein X is a halogen atom, in the presence of a base with a compound of the formula

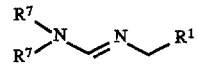

wherein $R^7$ is lower alkyl or cycloalkyl and $R^1$ is as described above.

2. A process in accordance with claim 1, wherein $R^1$ is cyano.

3. A process in accordance with claim 1, wherein $R^1$ is —COOR$^4$.

4. A process in accordance with claim 3, wherein $R^4$ is ethyl.

5. A process in accordance with claim 1, wherein $R^2$ is hydrogen and $R^3$ is methyl.

6. A process in accordance with claim 1, wherein A is a group (a).

7. A process in accordance with claim 6, wherein $R^5$ is hydrogen or fluorine and $R^6$ is hydrogen, fluorine, chlorine, or methyl.

8. A process in accordance with claim 7, wherein at least one of $R^5$ and $R^6$ is hydrogen.

9. A process in accordance with claim 8, wherein $R^5$ is fluoro and $R^6$ is hydrogen.

10. A process in accordance with claim 1, wherein the process is carried out at temperatures between −30° to −40° C.

11. A process in accordance with claim 1, wherein the base is lithium hexamethyldisilazide.

12. A process in accordance with claim 1, wherein the compound of formula I is ethyl-8-fluoro-5,6-dihydro-5-methyl-6-oxo-4H-imidazo-[1,5-a][1,4]benzodiazepine-3-carboxylate is prepared.

13. A process in accordance with claim 1, wherein the compound of formula I is 8-fluoro-5-methyl-6-oxo-4H-imidazo[1,5-a][1,4]benzodiazepine-3-carbonitrile.

* * * * *